United States Patent
Peszynski et al.

(10) Patent No.: US 7,052,463 B2
(45) Date of Patent: May 30, 2006

(54) METHOD AND APPARATUS FOR COOLING A CONTACTING SURFACE OF AN ULTRASOUND PROBE

(75) Inventors: Michael Peszynski, Newburyport, MA (US); John J. Merlo, Bedford, MA (US); Matthew Robert Rielly, Seattle, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 113 days.

(21) Appl. No.: 10/254,249

(22) Filed: Sep. 25, 2002

(65) Prior Publication Data

US 2004/0059226 A1    Mar. 25, 2004

(51) Int. Cl.
A61B 8/00    (2006.01)

(52) U.S. Cl. .............. 600/459; 600/437; 600/462; 600/466; 600/467; 600/471; 600/439

(58) Field of Classification Search ........ 600/437–472; 601/1–5
See application file for complete search history.

(56) References Cited

U.S. PATENT DOCUMENTS

| | | | |
|---|---|---|---|
| 4,748,985 A * | 6/1988 | Nagasaki | 600/445 |
| 5,427,106 A | 6/1995 | Breimesser et al. | 128/661.01 |
| 5,560,362 A * | 10/1996 | Sliwa et al. | 600/439 |
| 5,620,479 A | 4/1997 | Diederich | 607/97 |
| 5,721,463 A | 2/1998 | Snyder | 310/334 |
| 5,732,707 A * | 3/1998 | Widder et al. | 600/458 |
| 5,935,124 A | 8/1999 | Klump et al. | 606/42 |
| 5,961,465 A | 10/1999 | Kelly, Jr. et al. | 600/459 |
| 6,053,912 A | 4/2000 | Panescu et al. | 606/40 |
| 6,083,166 A * | 7/2000 | Holdaway et al. | 600/439 |
| 6,113,543 A * | 9/2000 | Bonnefous | 600/438 |
| 6,126,619 A * | 10/2000 | Peterson et al. | 601/2 |
| 6,436,130 B1 * | 8/2002 | Philips et al. | 607/105 |
| 6,521,211 B1 * | 2/2003 | Unger et al. | 424/9.52 |
| 2002/0022833 A1 | 2/2002 | Maguire et al. | 606/27 |

FOREIGN PATENT DOCUMENTS

| WO | WO0205897 | 1/2002 |
|---|---|---|
| WO | WO2056780 | 7/2002 |

* cited by examiner

Primary Examiner—Ali Imam
Assistant Examiner—William Jung

(57) ABSTRACT

A cooling system for an ultrasonic imaging system is provided, the ultrasonic imaging system having a probe for transmitting and receiving acoustic signals through a tip of the probe to and from biological tissue contacting the tip at an outer surface of the tip. The cooling system includes a conduit for circulating cooling medium therein, and a heat exchanger in fluid communication with the circulating cooling medium and having means for removing heat from the circulating cooling medium, wherein at least a portion the conduit is in proximity to or contacts the outer surface of the probe tip. In a first embodiment the conduit includes an inlet fluid line extending from the heat exchanger to the tip of the probe for providing the circulating cooling medium from the heat exchanger to the probe tip, and an outlet cooling line extending from the tip of the probe to the heat exchanger for providing circulating cooling medium from the probe tip to the heat exchanger. In a second embodiment the heat exchanger is housed in the probe. In a third embodiment, the probe is housed within a housing, wherein a portion of the conduit extends from the tip of the probe along an external surface of the housing.

18 Claims, 6 Drawing Sheets

METHOD AND APPARATUS FOR COOLING A CONTACTING SURFACE OF AN ULTRASOUND PROBE

FIELD OF THE INVENTION

The present invention generally relates to imaging probes, and in particular to a system and method for cooling a tip of the imaging probes.

BACKGROUND OF THE INVENTION

Ultrasound diagnostic technology generally relates to imaging of biological tissue using an ultrasonic transducer probe. The probe includes a transducer which transmits ultrasonic waves and receives ultrasonic echoes reflected from the tissue. The transducer is typically placed on the body surface or internal to a body lumen of a patient in a selected imaging region. The ultrasound transducer generates and directs ultrasonic waves to the imaging region. The transducer then receives ultrasonic waves reflected from the region and converts the received waves into electrical signals that are processed to form a diagnostic image.

A thermal build-up is created in the probe during transmission due to acoustic losses being converted into heat. Prescribed limits are set or prescribed by governing agencies as to the amount of heat that can be allowed to build up on the surface of the probe, typically limiting the surface temperature of the probe tip to a predetermined temperature or to a predetermined increase above ambient temperature, and hence limiting the acoustic output. Optimal transducer performance is obtained when the surface temperature of the probe tip is maintained at a specified temperature, such as ambient temperature, regardless of the acoustic output.

Various methods have been proposed for thermal management in ultrasonic probes. Conventional methods prescribe passive cooling of the transducer structure by transferring heat from the source into the body and handle of the probe. U.S. Pat. No. 5,560,362 to Sliwa Jr. et al. teaches active cooling by using an open loop cooling system, a closed loop circulating cooling system, a thermoelectric cooling system and an evaporator/condenser system. U.S. Pat. No. 5,721,463 to Snyder teaches transferring heat from the transducer structure through cable components used as heat conductors, and in an alternate embodiment where the cable components include a circulating cooling system. U.S. Pat. No. 5,961,465 to Kelly Jr. et al. teaches transferring of heat from integrated circuits located within the housing of the probe and approximate the transducer, where the transfer of heat is provided by a circulating cooling system.

The above methods transfer heat away from, or cool, the portion of the transducer structure that is internal to the probe, and therefore remote from the biological tissue being imaged. However, the primary source of heat generation is the area of the probe closest to the biological tissue, namely, the area of the transducer from which the acoustic energy is transmitted towards the biological tissue, and the adjacent lens in contact with the biological tissue through which the acoustic energy is focused and directed into the biological tissue. Therefore, a need exists for a method to transfer heat from, or cool, the area of the probe that is in contact with the biological tissue, i.e., tip of the probe, for transferring heat from the source of heat generation and for controlling the temperature at the point where temperature limits are prescribed.

U.S. Pat. No. 5,721,463 further teaches a thermal enhancement layer consisting of a film of diamond or diamond-like carbon-based material, which is highly thermally conductive, formed on the acoustic components at the distal end of the probe. However, the diamond film must be extremely thin for adequate acoustic coupling, which limits its ability to thermally couple with the biological tissue. Furthermore, the thermal conduction of the diamond film is fixed and not adjustable. Additionally, the heat being transferred is transferred either from the probe to the biological tissue, or vice versa; both methods of which defy the purpose of the heat transfer. Thus, a need continues to exist for transferring heat from, or cooling, the tip of an imaging probe for providing improved acoustic and thermal coupling.

SUMMARY OF THE INVENTION

A cooling system for an ultrasonic imaging system is provided, the ultrasonic imaging system having a probe for transmitting and receiving acoustic signals through a tip of the probe to and from biological tissue contacting the tip at an outer surface of the tip. The cooling system includes a conduit for circulating cooling medium therein, and a heat exchanger in fluid communication with the circulating cooling medium and having means for removing heat from the circulating cooling medium, wherein at least a portion the conduit is in proximity to or contacts the outer surface of the probe tip.

Preferably, the cooling medium further includes circulation apparatus for enabling circulation of the circulating cooling fluid within the conduit, and a control system having a sensor positioned at the outer surface of the probe tip and a processor adapted for receiving signals from the sensor and controlling at least one of the circulation apparatus and the heat exchanger.

In a first embodiment the conduit includes an inlet fluid line extending from the heat exchanger to the tip of the probe for providing the circulating cooling medium from the heat exchanger to the probe tip, and an outlet cooling line extending from the tip of the probe to the heat exchanger for providing circulating cooling medium from the probe tip to the heat exchanger. Preferably, a first membrane is coupled to the outer surface of the tip; a second membrane is connected to the periphery of the first membrane forming a cavity between the first and second membranes; the inlet cooling line is in fluid communication with the cavity and the heat exchanger for providing the circulating cooling medium from the heat exchanger to the cavity, and the outlet cooling line in fluid communication with the cavity and the heat exchanger for providing the circulating cooling medium from the cavity to the heat exchanger.

In a second embodiment the heat exchanger is housed in the probe. In a third embodiment, the probe is housed within a housing, wherein a portion of the conduit extends from the tip of the probe along an external surface of the housing.

BRIEF DESCRIPTION OF THE DRAWINGS

Various embodiments of the invention will be described herein below with reference to the figures wherein.

DESCRIPTION OF THE PREFERRED EMBODIMENTS

Figure 1:
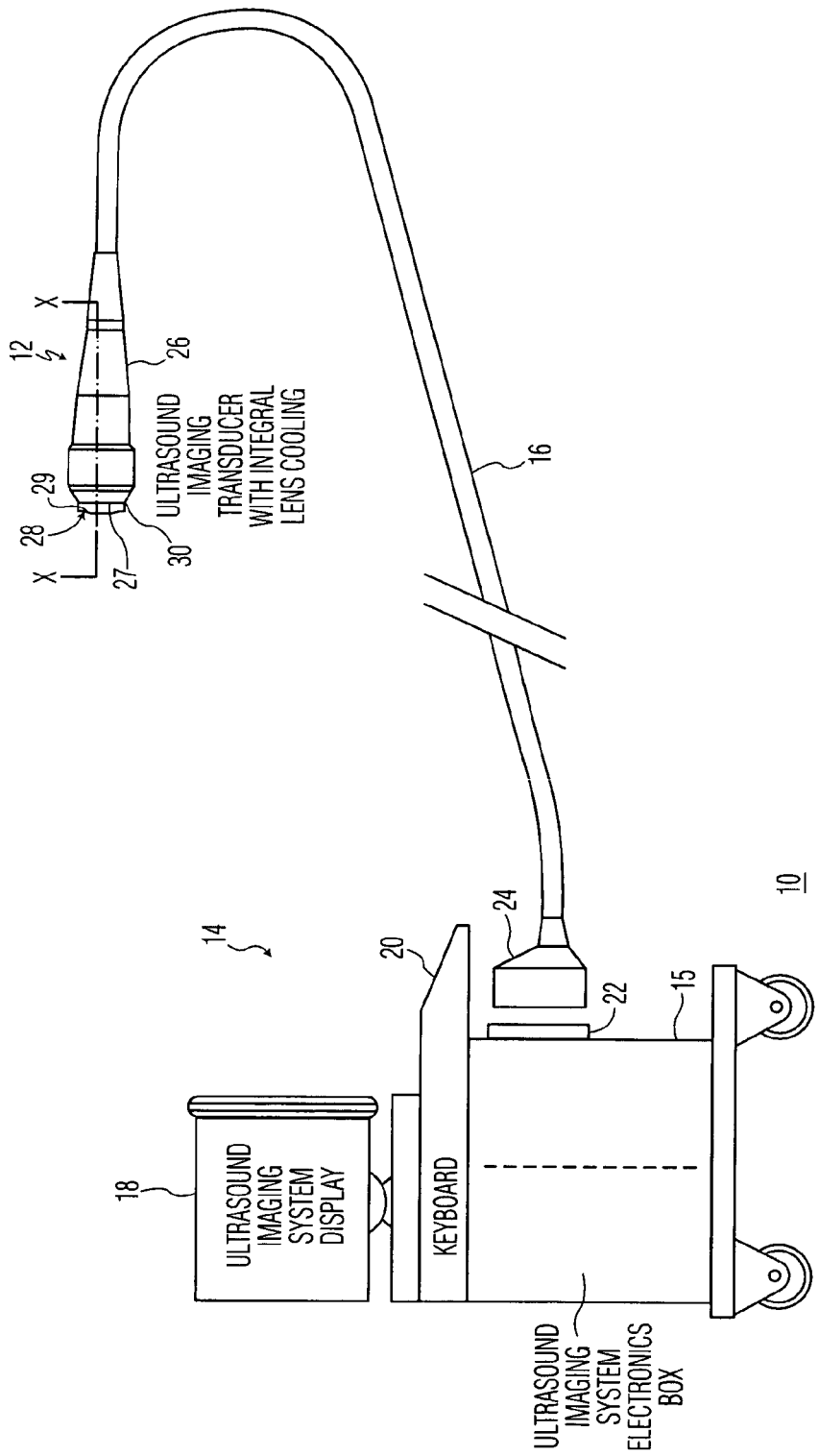
FIG. 1 is a schematic representation of an ultrasonic system in accordance with the present invention.

Referring to FIG. 1, an ultrasonic imaging system 10 is shown suitable for delivering ultrasonic waves to biological tissue and receiving echoes from the biological tissue via probe 12. The ultrasonic imaging system 10 includes probe 12 having a transducer (not shown), ultrasound console 14 and cable 16 for connecting the probe 12 and the console 14. Console 14 includes an electronics box 15 housing a processor (not shown) for processing signals received from the probe 12 and for controlling the probe 12, an ultrasound imaging system display 18, a user interface, such as keyboard 20, for allowing a user to input data, and a first connector 22 for receiving cable 16. Cable 16 includes a second connector 24 at its proximal end for mating with first connector 22 of the console 14. First and second connectors 22, 24 include mating transducer connectors, respectively, for transferring signals between the transducer and the processor within the console 14.

The probe 12 includes a handle 26 housing the transducer as well as other internal components. The handle 26 is graspable by a technician during an imaging session. A cooling conduit system 28 is provided integrated with the probe 12, where only a portion of cooling conduit system 28 is shown in FIG. 1. At least a portion of the cooling conduit system 28 is in surface to surface contact at surface 27 of the cooling conduit system 28 with the outer surface 27 of tip 30 of the probe 30, i.e., the distal end of the probe 30, where the outer surface 29 contacts the biological tissue during an imaging session. A cooling medium passes through the cooling conduit system over the tip 30, at the outer surface 29 of tip 30, for transferring heat from the tip 30.

The cooling medium is a medium capable of flowing through the cooling conduit system 28 and having good thermal conductivity and acoustic transparency. The cooling medium is preferably a liquid, such as water. Preferably, a conduit of the cooling conduit system 28 through which a liquid cooling medium flows is purged of air. Preferably, the conduit is provided with a bubble trap or air bleed valve for removing air from or preventing entry of air into the conduit. It is contemplated that the cooling medium may be a gas or a slurry having the required acoustic properties and thermal conductivity.

Figure 2:
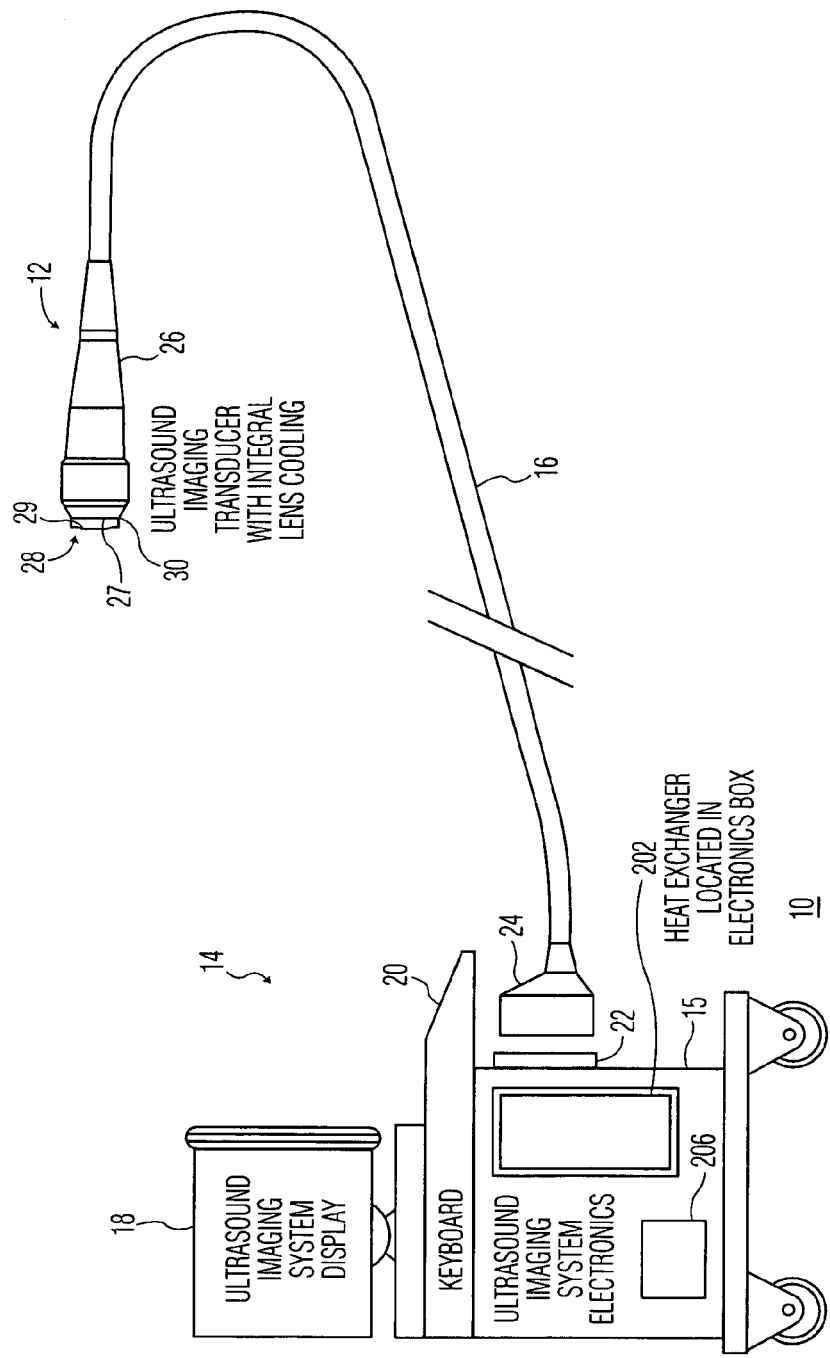
FIG. 2 is a schematic representation of an ultrasonic system in accordance with a first embodiment of the present invention.

FIG. 2 shows a first embodiment of the present invention in which the cooling conduit system 28 further includes a heat exchanger 202 housed in console 14, and conduits extending through cable 16. A cooling medium passes through the cooling conduit system 28 over the tip 30 of the probe 12 for transferring heat from the tip 30 of the probe 12, away from the tip 30 of the probe 12, through the conduits extending through cable 16, and to the heat exchanger 202. At the heat exchanger 202, a heat sink is provided for removing heat from the cooling medium. The cooled cooling medium then flows through the conduits in cable 16 to the tip 30 of the probe 12.

The heat exchanger 202 uses heat removal methods that are known to one skilled in the art, such as thermoelectric cooling, evaporative cooling, circulation, etc. Circulation may be passive or active. Active circulation is implemented using conventional circulating means, such as a pump, fan or suction means employing negative pressures, included in the cooling conduit system 28. Preferably, the circulating means is provided at the heat exchanger 202. It is contemplated that at the heat exchanger 202 the warmed cooling medium is disposed of and a fresh supply of cooled cooling medium is supplied.

The first and second connectors 22 and 24 include first and second mating cooling medium connectors (not shown), respectively, for providing a simple means for connecting and disconnecting the cable 16 from the console 14, so that a path for the cooling medium between the conduits of the cable 16 and the exchanger 202 is provided when the cable is connected to the console 14.

The cooling conduit system 28 is preferably further provided with a sensor(s) (not shown) and a control module 206. The sensors are preferably temperature sensing devices, such as a thermister or a thermocouple, and are strategically positioned integrally within the probe for proper sensing of the bio-tissue contacting surface 29 of the tip 30 which is being monitored without producing an image artifact. Preferably, the control module 206 is housed in console 14, however the control module 206 may be located at another location within the ultrasonic imaging system 10. The control module 206 receives signals from the sensor and transmits signals to the heat exchanger 202 and/or circulation means for controlling degree of cooling and/or the rate of flow of the cooling medium in order to maintain a constant temperature at the contacting surface of the tip 30.

Figure 3:
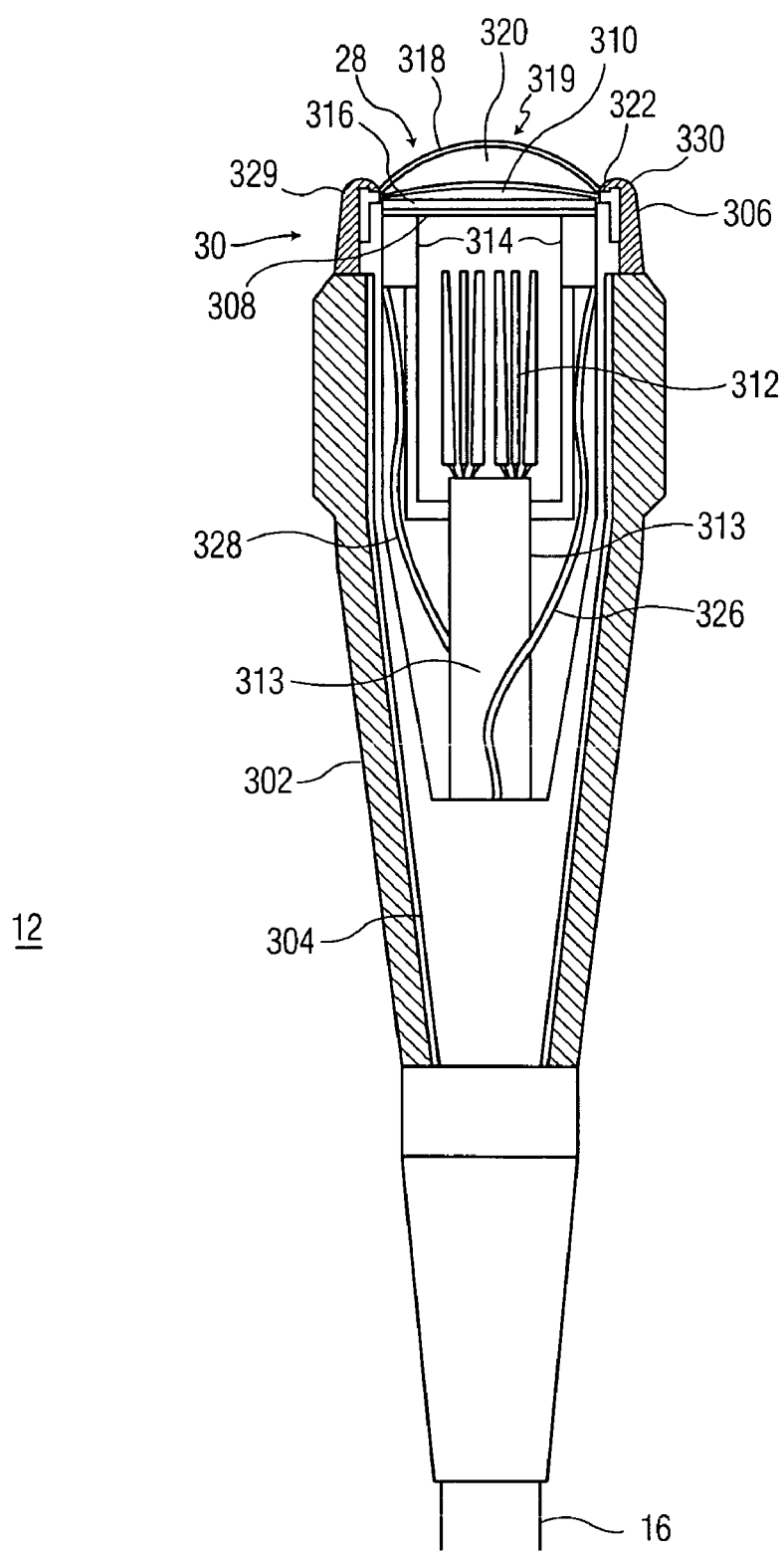
FIG. 3 is a cross-sectional side view taken along line X—X of an ultrasonic probe in accordance with the first embodiment of the present invention.

With reference to FIG. 3, the probe 12 of the first embodiment is shown with a portion of the cooling conduit system 28 integral within probe 12 at the outer surface of tip 30 of the probe 12. The probe includes housing 302, inner frame 304 and transducer cap retainer 306. Housed within the transducer cap retainer 306 is an array stack 308 of transducer elements forming the transducer, and an acoustic lens 310 positioned at the tip of the probe 12, and forming the outer surface of the tip 30, for directing the acoustic energy towards the biological tissue. The array stack 308 is an array stack that is known in the art, for example, a linear array, a curvilinear array, and an array stack of one or more one-dimensional or two-dimensional array stacks which may be static or have mechanical transducers. The probe 12 may be formed without an acoustic lens 310 or with the acoustic lens 310. Additional structures may be included at the tip 30, such that the outer surface of tip 30 is other than the acoustic lens 310. The outer surface of the tip 30 may be static or may be in motion, such as rotating.

Housed within the housing 302 are cable interconnects 312 and ultrasound cable 313. Interconnects 312 provide a connection between the array stack 308, as well as other electronic devices 314, such as integrated circuits, and the ultrasound cable 313. The ultrasound cable 313 exits the housing 302 at a proximate end of the housing, from where it extends through the cable 16 to the console 14, as shown in FIG. 2. Signals being transferred between the ultrasound cable 313 and the console 14 are transferred via connectors 22, 24 shown in FIGS. 1 and 2.

Integration of the cooling conduit system 28 into the probe 12 will now be described. A first layer of acoustically clear material 316, such as polyethylene, is bonded or coupled to the outer surface of the tip 30 so that the acoustically clear material 316 is acoustically and thermally coupled to the outer surface of the tip 30. A second layer of acoustically clear material 318, such as polyethylene, is bonded, sealed or connected at its periphery to the first layer of acoustically clear material 316 forming a pocket 319 having a cavity 320 between the first and second layers of acoustically clear material 316, 318. The acoustically clear material 316 is coupled or bonded to the outer surface of the tip 30, such as by a thin acoustically transparent bonding material or by capillary action, such as of a suitably acoustically clear liquid.

The cavity 320 is filled with the cooling medium. The cavity 320 communicates via cooling medium inlet 322 and cooling medium outlet 324 with inlet cooling line 326 and outlet cooling line 328, respectively. Cooling medium seals 330 are provided at the cooling medium inlet 322 and outlet 324 for reducing or stopping flow of the cooling medium. The inlet cooling line 326 and outlet cooling line 328 exit the housing 302 and extend through the length of the cable 16 and connect to the heat exchanger 202 via cooling medium connectors within connectors 22, 24, as shown in FIG. 2.

With reference to FIGS. 2 and 3, cooled cooling medium flows from the heat exchanger 202 through the cooling medium connectors of first and second connectors 22, 24 to the inlet cooling line 326. The cooled medium fluid enters the cavity 320 through the cooling medium inlet 322. Heat generated at the acoustic lens 310 is transferred via thermal coupling to the cooling medium in the cavity 320. The heated cooling medium flows through cooling medium outlet 324 to outlet cooling line 328, from where the heated cooling medium enters the heat exchanger 202 via the cooling medium connectors of first and second connectors 22, 24. Within the heat exchanger 202 the heated cooling medium is cooled.

Preferably the first layer of acoustically clear material 316 is formed of a flexible material for providing maximum thermal and acoustical coupling. Preferably, second layer of acoustically clear material 318 contacting the biological tissue provides acoustical coupling and/or lubricating between the acoustic lens 310 and the biological tissue.

It is contemplated that the first layer of acoustically clear material 316 is removably bonded, sealed or connected to the acoustic lens 310, and that the cooling medium inlet and outlet 322, 324 are sealable, thus allowing for removal from the probe 12 of the portion of the cooling conduit system 28 that is external to the probe 12, i.e., the pocket 319. Sterilization procedures may be performed without being compromised or complicated by the cooling conduit system 28. Furthermore, it is contemplated that the pocket 319 is disposable and replaceable.

Figure 4:
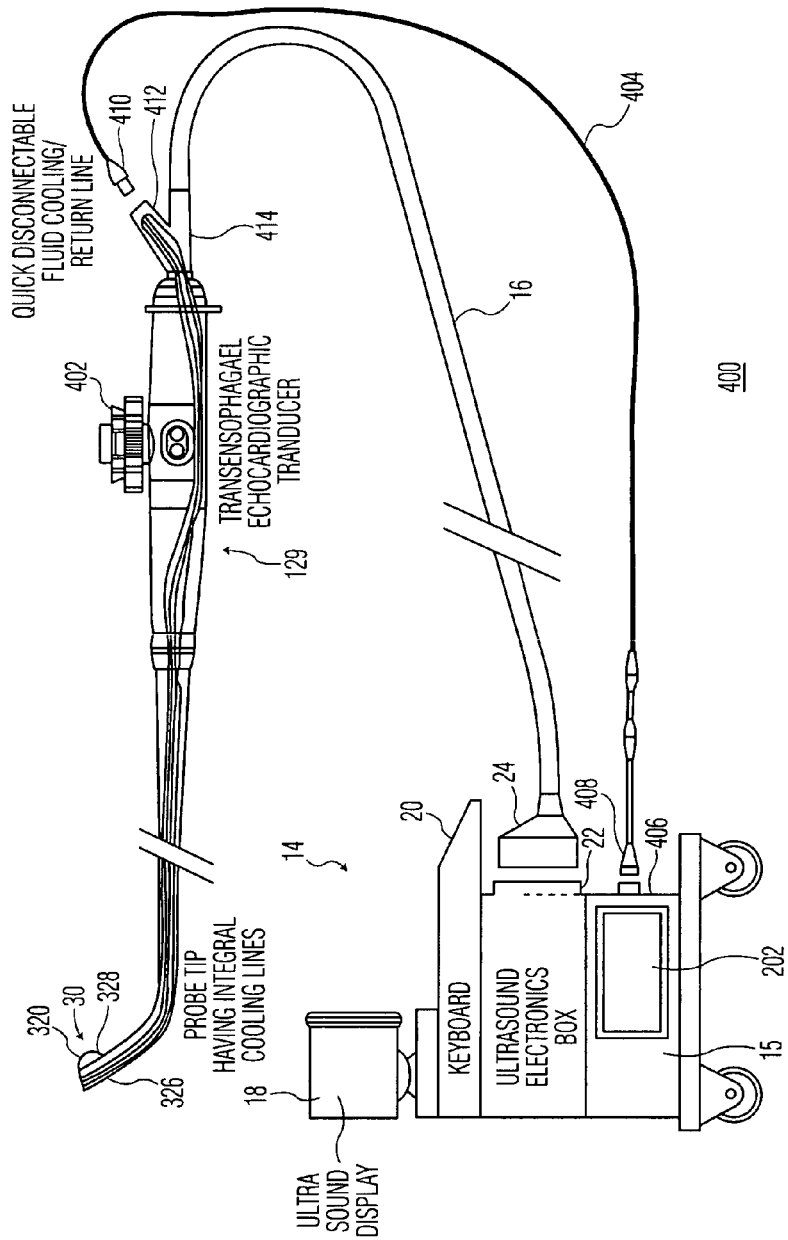
FIG. 4 is a schematic representation of an ultrasonic system in accordance with a second embodiment of the present invention.

With reference to FIG. 4, ultrasound imaging system 400 is shown, illustrating a second embodiment of the invention. The probe shown is a Trans-Esophageal Echocardiographic (TEE) probe. However, other types of probes may be substituted. The TEE probe includes an elongated distal end portion and probe tip articulation controls 402. The inlet cooling line 326 and outlet cooling line 328 extend from the tip 30 to the proximate end of the probe 12A. A fluid connector line 404 is provided for providing respective paths between the inlet and outlet cooling lines 326, 328 and the console 14. Cable 16 is a conventional cable for housing the ultrasound cable 313 having connectors 22, 24 for transferring signals between the console 14 and the probe 12A.

The fluid connector line 404 and heat exchanger 202 are provided with mating connectors 406 and 408, respectively, for allowing exchange of the cooling medium between the fluid connector line 404 and the heat exchanger 202. The fluid connector line 404 and the proximate end of the probe 12A are provided with mating connectors 410 and 412, respectively, for allowing exchange of the cooling medium between the fluid connector line 404 and the inlet and outlet cooling lines 326, 328 of the probe 12A. The proximate end of the probe 12A is provided with a forked portion 414 with a first branch provided with connector 412 and a second branch provided with a connector for connecting to cable 16. Preferably, connectors 406, 408, 410, 412 are suitable for quick connection and disconnection. In an alternate embodiment, the heat exchanger 202 may be located in the handle of the probe 12A.

Figure 5:
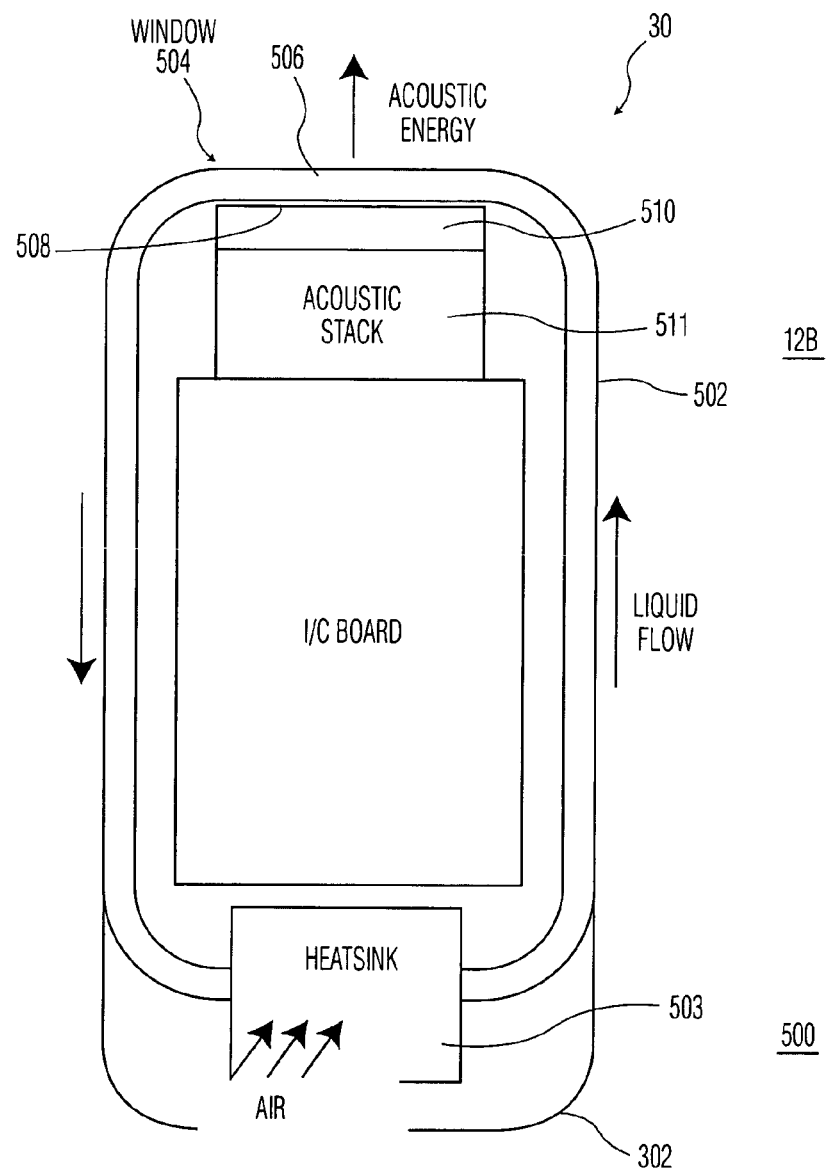
FIG. 5 is a top view of a tip portion of the probe of FIG. 3, shown in greater detail.

With reference to FIG. 5, a cooling conduit system 500 for a probe 12B of an ultrasonic imaging system is shown in a third embodiment. Conduit cooling system 500 includes a conduit 502 through which the cooling medium flows and heat exchanger 503 for providing a heat sink for the flowing cooling medium. The conduit passes over the outer surface of the tip 30 of probe 12B. The portion of the conduit 502 positioned directly above acoustic lens, or other structure located at the outer surface of the tip 30, through which the acoustic energy is transmitted and received forms a window 504.

The conduit 502 is formed of a single tube shaped membrane coupled or bonded to existing materials within the probe 12B, and the cooling medium flows through a conduit formed within the tube. Top and bottom surfaces 506, 508, respectively, of the window 504 are formed of the portion of the tube shaped membrane located directly above an acoustic lens 510, or in the absence of a lens, directly above the final layer in the acoustic stack 511 such that the transmitted acoustic energy passes through two layers of the membrane. The bottom layer of the membrane lying on the acoustic lens 510, or other structure located at the outer surface of the tip 30, is bonded or coupled thereto with a bonding or coupling that is acoustically transparent, such as by a thin acoustically transparent bonding material or by capillary action, such as of a suitably acoustically clear liquid.

In an alternate embodiment, the conduit 502 is formed, at least partially, of a membrane coupled or bonded to existing materials within the probe 12B, and the cooling medium flows through the conduit formed between the membrane and the existing materials. A fluid cavity positioned in the window 504 is constructed such that the cooling medium is bounded by the acoustic lens 510 (or in absence of an acoustic lens, by the final layer in the acoustic stack 511 or other structure located at the outer surface of the tip 30) and the membrane of the conduit 502 that is in contact with the tissue. In this embodiment, the bottom surface 508 of the window 504 is the top surface of the acoustic lens 510, or in the absence of a lens the final layer in the acoustic stack 511 or other structure of the probe 12B located at the outer surface of the tip 30, and the top surface 506 of the window 504 is the bonded membrane, so that the transmitted acoustic energy passes through one layer of the membrane.

The top and bottom surfaces of the window 504 are acoustically transparent. The bottom surface of the window 504 provides thermal coupling between the acoustic lens 510 and the cooling medium flowing through conduit 502. Preferably, the top surface of the window 504 provides acoustical coupling and/or lubricating between the window 504 and the biological tissue. Preferably, the membrane of both embodiments of conduit 502 is flexible for providing maximum thermal and acoustical coupling.

The heat exchanger 503 uses heat removal methods that are known to one skilled in the art, such as thermoelectric cooling, evaporative cooling, circulation, etc. The exemplary heat exchanger 503 is provided in the form of an air-cooled heat sink. The air may be condensed air further lowering the temperature of the cooling medium. Direction of the flow of air may be opposite to the direction shown for directing warmed air away from the tip 30. The conduit 502 may be a continuous conduit which passes through or by the heat exchanger 503. Alternatively, the conduit 502 may have an open end at opposite sides of the heat exchanger 503, allowing the cooling medium to flow through the heat exchanger 503 for transferring heat from the cooling medium. The heat exchanger 503 may be configured to use heat removal methods that are known to one having average skill in the art, such as thermoelectric cooling, evaporative cooling, circulation, etc.

In one embodiment induced flow is not necessary. The conduit 502/heat exchanger 503 is a closed system in which free convection causes sufficient mixing allowing adequate heat transfer from the tip 30. Circulation via free convection depends on the orientation of the probe 12B. If needed, a conventional circulating means, such as a pump, fan or suction means employing negative pressures, is included in the cooling conduit system 500.

It is contemplated that the cooling conduit system 500 includes sensors and a control module receiving signals from the sensors for controlling the heat exchanger 503 and/or circulation means for controlling degree of cooling and/or the rate of flow of the cooling medium in order to maintain a constant temperature at the contacting surface of the tip 30. The sensors are strategically positioned integrally within the transducer construction for proper sensing of the bio-tissue contacting surface of the tip 30 without producing an image artifact. The control module may be housed within one or more components of the ultrasonic imaging system, such as the probe 12B or the console 14 (shown in FIG. 1) or external thereto. It is further complicated that the conduit 502 is removable and replaceable for providing easy sterilization.

Figure 6:
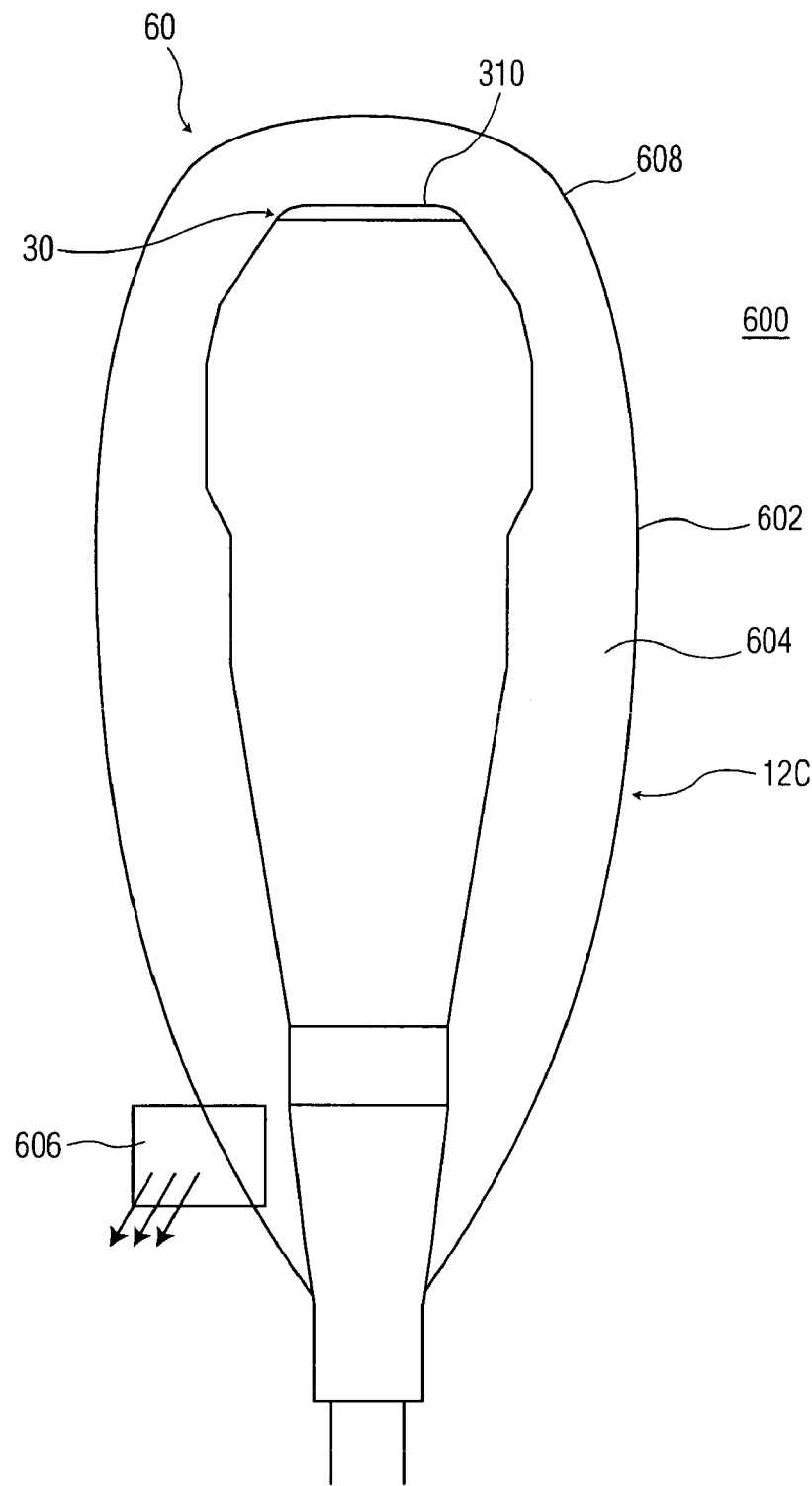
FIG. 6 is a side view of a probe of an ultrasonic system in accordance with a third embodiment of the present invention.

With reference to FIG. 6, a probe 12C having an external cooling system 600 is shown. The cooling system 600 includes a sealed pocket 602 having a cavity 604 for holding the cooling medium and a heat exchanger 606 for providing a heat sink for removing heat from the cooling medium. Preferably, the pocket 602 is filled with a liquid which is purged of air. Preferably, the pocket is provided with a bubble trap or air bleed valve for removing air from or preventing entry of air into the pocket.

The pocket 602 is secured to the probe 12C so that a portion of the pocket is coupled with the outer surface of the tip 30 (i.e. the outer surface of the acoustic lens 310 in the example shown) of the probe 12C. The pocket is be coupled or bonded to the outer surface of the tip 30 with a bonding or coupling that is acoustically transparent. The portion of the pocket lying over the acoustic lens 310 forms a window 610 that is transparent to acoustic energy. The cooling medium is circulated within the pocket for withdrawing heat from the tip 30 of the probe 12C.

The pocket is secured to the housing of the probe 12C by conventional means such as an adhesive or a fastener. The pocket is formed of a layer of material 608 that is not permeable to the cooling medium. The layer of material 608 may be formed of one or more layers of material joined together. Preferably, the pocket 602 forms a sheath which fits over the probe 12C. The entire layer of material 608, or at least the portion thereof forming the window 610, is formed of an acoustically clear material. At least the portion of the layer of material 608 contacting the acoustic lens 310 is formed of a good thermal conductor. Preferably the portion of the layer of material 608 forming the window 610 is formed of a flexible material for providing maximum thermal and acoustical coupling. Preferably, the portion of the layer of the material 608 contacting the biological tissue provides acoustical coupling and/or lubricating between the window 610 and the biological tissue.

The heat exchanger 606 uses heat removal methods that are known to one skilled in the art, such as thermoelectric cooling, evaporative cooling, circulation, etc. Circulation of the cooling medium may be passive or active. Active circulation is implemented using conventional circulating means, such as a pump, fan or suction means employing negative pressures, included in the cooling conduit system 600. Preferably, the circulating means is provided at the heat exchanger 606.

The pocket 602 may provide a continuous conduit which passes through or by the heat exchanger 606. Alternatively, the conduit pocket 602 may have an inlet and outlet for allowing the cooling medium to flow through the heat exchanger 606.

It is contemplated that the cooling conduit system 600 includes sensors and a control module receiving signals from the sensors for controlling the heat exchanger 606 and/or circulation means for controlling degree of cooling and/or the rate of flow of the cooling medium in order to maintain a constant temperature at the outer surface of the tip 30. The sensors are strategically positioned integrally within the transducer construction for proper sensing of the bio-tissue contacting surface of the tip 30 without producing an image artifact. The control module may be housed within one or more components of the ultrasonic imaging system, such as the probe 12C or the console 14 (shown in FIG. 1) or external thereto. It is further complicated that the pocket 602 is removable from the probe 12C and replaceable for sterilization purposes.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

The invention claimed is:

1. A cooling system for an ultrasonic imaging system having a probe for transmitting and receiving acoustic signals to and from biological tissue contacting the probe, the cooling system comprising:
   a removable pocket defining a cavity therein and removably mounted to a distal end of the probe, the removable pocket having a tip for transmitting and receiving the acoustic signals therethrough to and from the biological tissue contacting the tip at an outer surface of the tip, the removable pocket further having a first opening and a second opening;
   a conduit for circulating cooling medium therein, said conduit including a cooling medium inlet and cooling medium outlet respectively communicating with an inlet cooling line and outlet cooling line of said conduit for flowing the cooling medium to and from the cavity at the distal end of the probe via the first and second openings, respectively;
   a cooling medium seal within the probe and in proximity to the cooling medium inlet for reducing or stopping flow of the cooling medium to the cavity via the first opening; and
   a heat exchanger located externally from the probe and in fluid communication with the circulating cooling medium via a cable housing a portion of the conduit, said heat exchanger having means for removing heat from the circulating cooling medium, wherein at least another portion of the conduit is in proximity to an external surface of the probe tip.

2. The cooling system in accordance with claim 1, wherein the conduit includes:
   a first membrane coupled to the outer surface of the tip;
   a second membrane connected to the periphery of the first membrane forming a cavity between the first and second membranes;
   an inlet cooling line in fluid communication with the cavity and the heat exchanger for providing the circulating cooling medium from the heat exchanger to the cavity; and
   an outlet cooling line in fluid communication with the cavity and the heat exchanger for providing the circulating cooling medium from the cavity to the heat exchanger.

3. The cooling system in accordance with claim 1, further comprising circulating means for enabling circulation of the circulating cooling fluid within the conduit.

4. The cooling system in accordance with claim 3, further comprising a control system having a sensor positioned at the outer surface of the probe tip and a processor adapted for receiving signals from the sensor and controlling at least one of the circulating means and the heat exchanger.

5. The cooling system in accordance with claim 1, wherein the ultrasound imaging system further includes a console having means for exchanging data with the probe, processing means for processing data to be transmitted and data received from the probe, display means for displaying data, and transmission means for transmitting data.

6. The cooling system in accordance with claim 5, wherein the conduit includes an inlet fluid line extending from the heat exchanger to the tip of the probe for providing the circulating cooling medium from the heat exchanger to the probe tip; and an outlet cooling line extending from the tip of the probe to the heat exchanger for providing circulating cooling medium from the probe tip to the heat exchanger.

7. The cooling system in accordance with claim 6, wherein the inlet and outlet cooling lines extend through a cable housing the transmission means.

8. An ultrasound imaging system comprising:
   a probe for transmitting and receiving acoustic signals to and from biological tissue contacting the probe;
   a housing for housing the probe; and
   a cooling system, the cooling system comprising:
     an inlet and an outlet line;
     a sealed pocket defining a cavity therein and removably mounted to a distal end of the probe, the sealed pocket having a tip for transmitting and receiving the acoustic signals therethrough to and from the biological tissue contacting the tip at an outer surface of the tip, the sealed pocket further having a first opening and a second opening for respectively receiving and dispensing a cooling medium from the inlet and outlet lines; and
     a heat exchanger in fluid communication with the inlet and outlet lines and having means for removing heat from the cooling medium.

9. The ultrasound imaging system in accordance with claim 8, wherein the sealed pocket is filled with the cooling medium and is substantially purged of air.

10. The ultrasound imaging system in accordance with claim 8, wherein the sealed pocket is removably coupled to the probe.

11. The ultrasound imaging system in accordance with claim 8, further comprising an acoustic lens positioned at a tip of the probe, wherein a portion of the sealed pocket lying over the acoustic lens forms a window that is transparent to acoustic energy.

12. The ultrasound imaging system in accordance with claim 11, wherein the sealed pocket is formed of a layer of material that is not permeable to the cooling medium.

13. The ultrasound imaging system in accordance with claim 12, wherein at least a portion of the material forming the window is formed of acoustically clear material.

14. The ultrasound imaging system in accordance with claim 12, wherein at least a portion of the material forming the window is formed of a flexible material.

15. An ultrasound imaging system comprising:
    a probe for transmitting and receiving acoustic signals through a tip of the probe to and from biological tissue contacting the probe tip at an outer surface of the probe tip; and
    a removable pocket defining a cavity therein and removably mounted to a distal end of the probe, the removable pocket having the tip for transmitting and receiving the acoustic signals therethrough to and from the biological tissue contacting the probe tip at the outer surface of the probe tip, the removable pocket further having a first opening and a second opening; and
    a cooling system, the cooling system comprising:
      a conduit for circulating cooling medium therein, said conduit including a cooling medium inlet and cooling medium outlet respectively communicating with an inlet cooling line and outlet cooling line of said conduit for flowing the cooling medium to and from the cavity at the distal end of the probe via the first and second openings, respectively;
      a cooling medium seal within the probe and in proximity to the cooling medium inlet for reducing or stopping flow of the cooling medium to the cavity via the first opening; and
      a heat exchanger located externally from the probe and in fluid communication with the circulating cooling medium via a cable housing a portion of the conduit, said heat exchanger having means for removing heat from the circulating cooling medium, wherein at least another portion of the conduit is in proximity to an external surface of the probe tip.

16. The ultrasound imaging system in accordance with claim 15, the cooling system further comprising circulating means for enabling circulation of the circulating cooling fluid within the conduit.

17. The ultrasound imaging system in accordance with claim 16, the cooling system further comprising a control system having a sensor positioned at the outer surface of the probe tip and a processor adapted for receiving signals from the sensor and controlling at least one of the circulating means and the heat exchanger.

18. The ultrasound imaging system in accordance with claim 15, wherein the probe is housed within a housing.

* * * * *